United States Patent [19]

Sarrine

[11] Patent Number: 5,195,534
[45] Date of Patent: Mar. 23, 1993

[54] BIOLOGICAL FLUID COLLECTION AND DISPENSING APPARATUS AND METHOD

[75] Inventor: Robert J. Sarrine, Beaumont, Tex.

[73] Assignee: Helena Laboratories Corporation, Beaumont, Tex.

[21] Appl. No.: 746,414

[22] Filed: Aug. 16, 1991

[51] Int. Cl.$^5$ .............................................. A61B 5/00
[52] U.S. Cl. ...................................... 128/764; 604/317
[58] Field of Search ........................ 128/760, 763–765, 128/770; 604/317, 403, 411, 415

[56] References Cited

U.S. PATENT DOCUMENTS 2,594,621  4/1952  Derrick ................................ 128/764
4,640,297  2/1987  Bates .................................... 128/765

FOREIGN PATENT DOCUMENTS 0017728  10/1980  European Pat. Off. ............ 128/764

Primary Examiner—Max Hindenburg
Attorney, Agent, or Firm—Spencer, Frank & Schneider

[57] ABSTRACT

A biological fluid collection and dispensing apparatus for attachment to a sealed test tube includes a pump and a housing, the housing having a movable portion, and a cannula assembly mounted relative to the housing. Biological fluid is withdrawn from a patient and flows through the pump and housing into the interior of the sealed test tube. The pump is actuated initially to release a delivery conduit and to move the housing such that part of the cannula assembly pierces the test tube seal. The pump is thereafter actuated to pressurize the contents of the test tube such that aliquots may be dispensed through the cannula assembly and delivery tube.

20 Claims, 3 Drawing Sheets

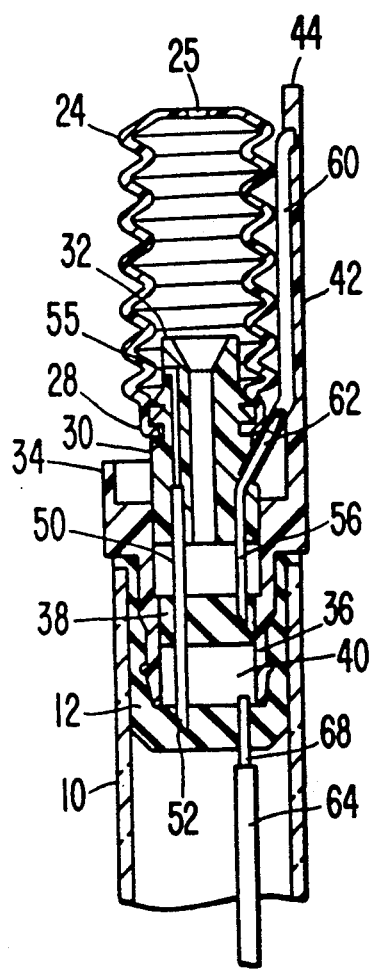
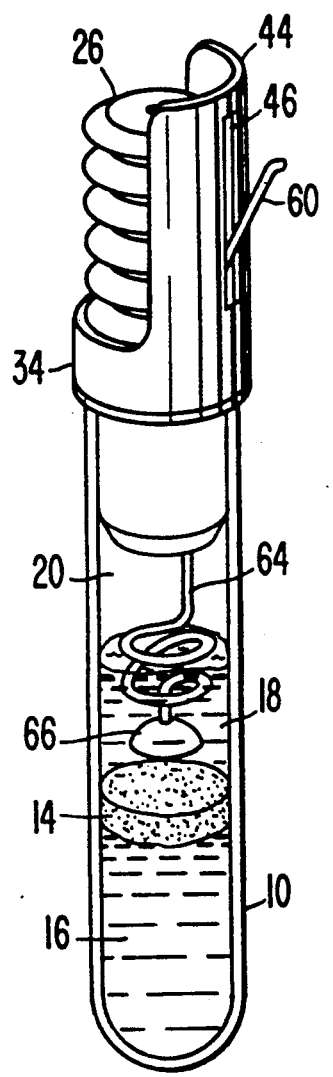
FIG. 1
FIG. 4

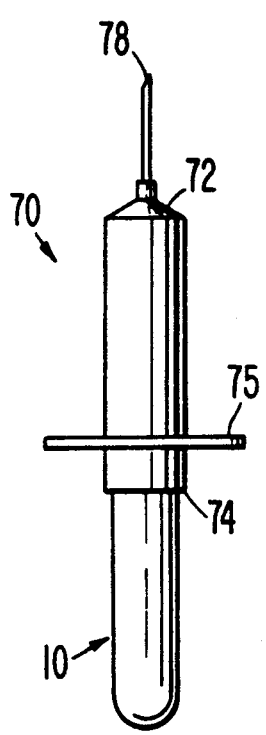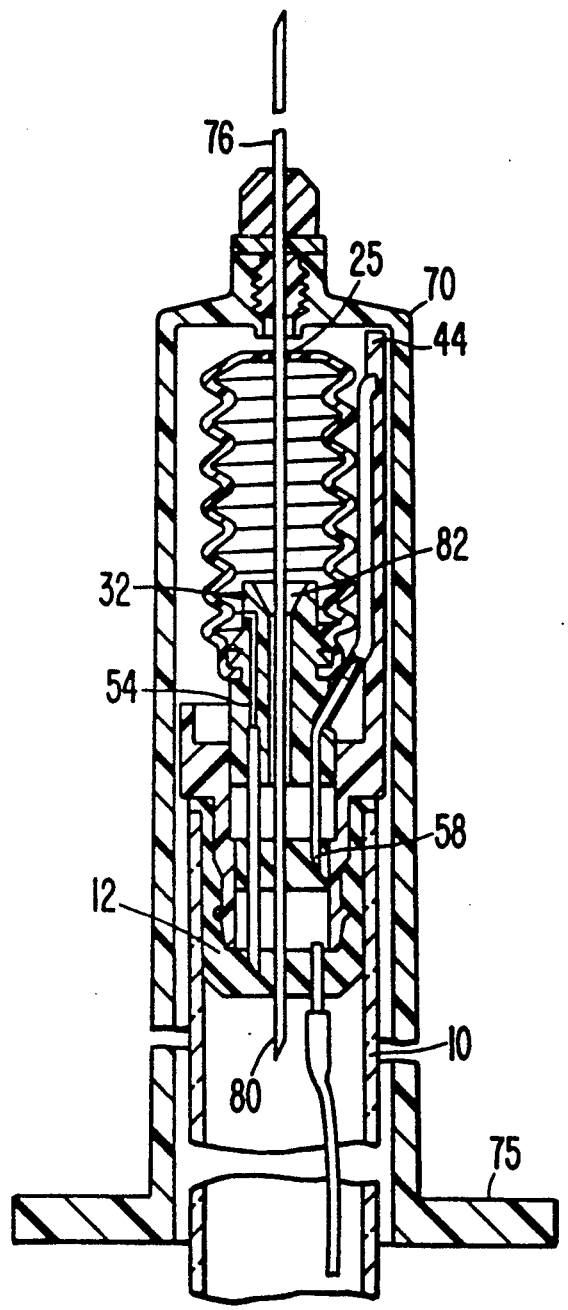

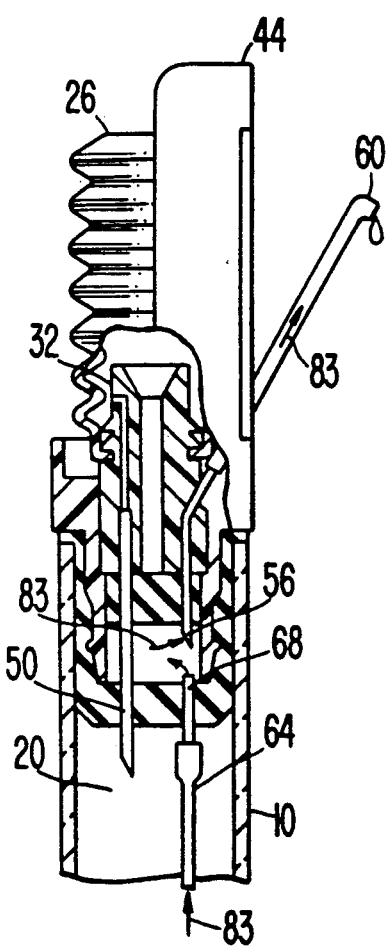
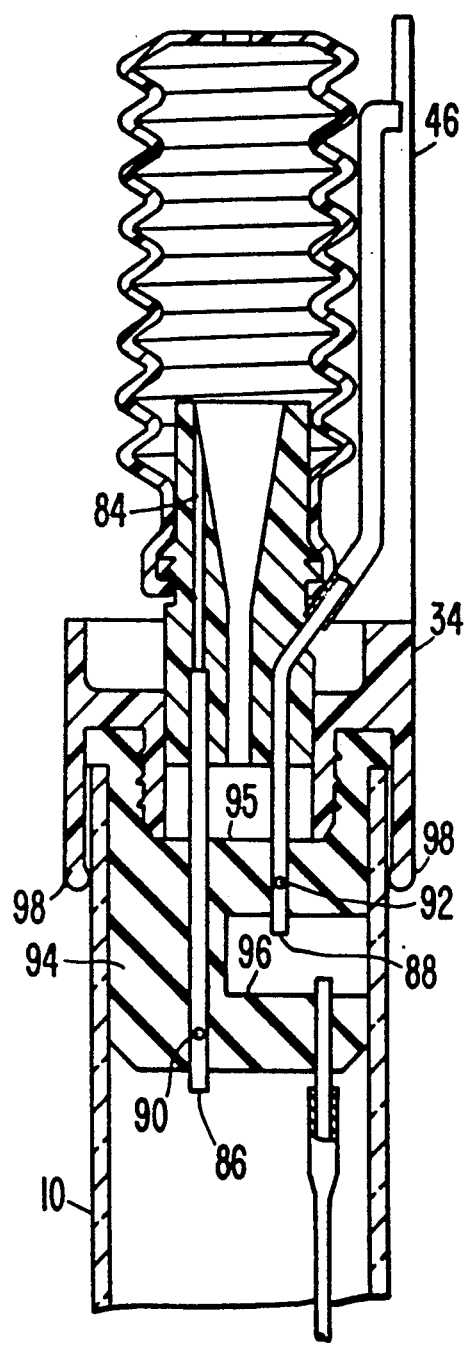

BIOLOGICAL FLUID COLLECTION AND DISPENSING APPARATUS AND METHOD

CROSS-REFERENCE TO RELATED APPLICATIONS

The present application includes subject matter in common with prior applications numbers Ser. No. 07/504,597, filed Apr. 4, 1990, which is a continuation-in-part of application Ser. No. 07/382,760, filed Jul. 21, 1989, which is a continuation-in-part of application Ser. No. 07/208,447 filed Jun. 20, 1988, and prior applications Ser. No. 07/256,243 filed Sep. 30, 1988, and Ser. No. 07/089,275 filed Aug. 25, 1987, now U.S. Pat. No. 4,925,065, which were continuations of Ser. No. 07/000,266 filed Jan. 2, 1987, now U.S. Pat. No. 4,811,866, all of which are hereby incorporated by reference.

BACKGROUND OF THE INVENTION

The present invention relates generally to methods and apparatus for drawing or collecting blood or other biological fluid from a patient and thereafter dispensing the biological fluid in aliquots for analytical testing. More specifically, the present invention relates to a one-piece disposable apparatus including all of the features needed to draw such fluid and thereafter dispense the fluid.

The separation and analysis of chemical substances provides valuable quantitative and qualitative data for use by researchers and health care providers. Many assaying techniques have been developed which utilize sensitive chemical tests and sensitive instruments to detect both normal and abnormal components of biological fluids such as blood, urine and spinal fluid. In particular, the analysis of samples of these fluids reveals information which is critical to the proper diagnosis and treatment of many disorders. To perform such an analysis, a biological sample is typically withdrawn from the patient into a test tube or vacuum draw collection tube. The biological sample may be centrifuged. Then, the biological sample is dispensed, in suitable aliquots, for testing. In the example of withdrawing blood from a patient, centrifugation separates the serum from the red blood cells and, thereafter, the amount of serum protein, protein-bound iodine, sodium, triglycerides, salicylate, uric acid and the like may all be determined through the analysis of the blood components.

After a biological sample is withdrawn from a patient into a test tube or collection tube, a technician must dispense aliquots or small quantity samples from the test tube. The test tube, of course, is initially sealed to prevent (a) contamination of the sample by ambient constituents and (b) to prevent substances in the sample from entering the atmosphere and/or adversely affecting the technician. Upon removing the conventional stopper from a test tube, the sample is again subject to possible contamination and a phenomenon known as aerosoling occurs. Aerosoling is the expulsion into the air, in the vicinity of the test tube, of minute quantities of the contents of the test tube and is caused by the force of removal of the stopper from the test tube. The removal of the stopper subjects the technician to the risk of exposure to whatever virus, bacteria or the like is carried in the biological sample.

The concern about exposure to the HIV virus has resulted in the adoption of numerous safety precautions in connection with the handling of biological fluids including products for dispensing biological fluids from a test tube without the need for removal of the stopper.

SUMMARY OF THE INVENTION

The present invention utilizes a new and different approach to the problems described above by eliminating the need for separate fluid withdrawal and fluid dispensing apparatus thus further minimizing the risk of contamination of the sample and further minimizing the risk of exposing the technician to the sample.

The present invention provides a new and improved apparatus which provides for both biological fluid withdrawal into a sealed container and biological fluid dispensing from the sealed container.

It is therefore an object of the invention to provide an efficient and inexpensive apparatus for biological fluid collection and dispensing.

It is a further object of the invention to provide a single assembly that performs both biological fluid collection and dispensing functions.

It is yet another object of the invention to provide a single apparatus for withdrawal of biological fluids such as blood, spinal fluids or the like into a sealed container, retaining such fluids for processing in the sealed container, and thereafter for dispensing the biological fluids in aliquots through the seal of the container.

The above and other objects are accomplished according to an embodiment of the invention by the provision of a biological fluid collection apparatus for attachment to a sealed test tube including a pump means mounted to a movable housing and cannula means mounted relative to the housing such that biological fluid is drawn through the pump means and housing and through the test tube seal into the test tube. The pump means may be actuated once to move the housing and, thereafter, on subsequent actuation of the pump means, biological fluid from the test tube is dispensed through the test tube seal and cannula means.

BRIEF DESCRIPTION OF THE DRAWINGS

The foregoing objects and advantages of the invention, together with other objects and advantages which may be attained by its use, will become more apparent upon reading the following detailed description of the invention taken in conjunction with the drawings. In the drawings, wherein like reference numerals identify corresponding components:

FIG. 1 is a cross-sectional view of an embodiment of the invention attached to a partially illustrated test tube;

FIG. 2 is an elevation view of a multiple draw blood collection holder and illustrating a test tube or blood collection tube positioned in the holder;

FIG. 3 is a cross-sectional view of the apparatus of the present invention inserted into the holder of FIG. 2;

FIG. 4 is a pictorial illustration of the apparatus of the present invention after biological fluid has been withdrawn from a patient and is ready to be dispensed;

FIG. 5 is a cross-sectional view of the apparatus of the present invention after biological fluid has been withdrawn from a patient and is ready to be dispensed; and FIG. 6 is a cross-sectional view of another embodiment of the present invention.

DETAILED DESCRIPTION OF THE INVENTION

Referring first to FIG. 1, the present invention is illustrated attached to a test tube or collection tube 10 of the type which is sealed by a puncturable, reusable, resilient stopper or closure 12 as is conventional. The sealed test tube may be under vacuum, such as a Vacutainer test tube marketed by BectonDickinson, and if the test tube is to be used for blood serum separation, then, in addition to an anticoagulant in the test tube as is conventional, a conventional gel-like separator plug 14 is included in the test tube. Referring briefly to FIG. 4, if blood has been introduced into the test tube and thereafter centrifuged, red blood cells 16 will be positioned in the bottom of the test tube, on one side of the separator plug 14, and serum 18 will be on the opposite side of the plug 14. An unfilled space or air gap 20 may exist between the serum and the underside of the stopper 12.

Pump means 24 is provided for dispensing the contents of the test tube. Specifically, a pump means is illustrated in the form of an elongated, flexible member such as a bellows or bulb having an aperture 25 in a first end 26 and a second end 28 secured to a circular groove 30 in the exterior of a housing means. The housing means includes a cylindrical plug 32 movably or slidably mounted within a stationary circular body 34 which has a lower, open cylindrical end 36. A first seal 38 is positioned within the body 34 and is recessed axially inwardly from the lower end 36. Thus an air gap or cavity 40 is defined as the region longitudinally between the seal 38 and the test tube stopper 12 and axially interiorly of the lower end 36 of the body. The circular body 34 includes an exterior wall 42 which extends from the body along the length of the bellows or pump in a direction away from the lower body end 36. The wall 42 is generally semicircular in configuration from the top of the plug to the top 44 of the wall; the circular body 34 and wall 42 may be formed as a one-piece member. An elongated vertical slot 46 extends through the wall 42.

Cannula means are provided for piercing the stopper such that biological fluid may be withdrawn from the test tube. The cannula means includes a first cannula 50, having a sharpened tip or end 52 which extends longitudinally of the pump means and through the seal 38. When the present invention is assembled to a test tube, the sharpened tip 52 is positioned in the test tube stopper but does not extend through the stopper. The first cannula 50 is connected through an elongated conduit 54 to the interior of the flexible pump or bellows. In the embodiment of FIGS. 1 and 3-5, conduit 54 is oriented parallel to the longitudinal axis of the housing and is connected to a conduit 55 which is at right angles to conduit 54. Conduit 55 is positioned to open interiorly of the pump means. Thus a fluid flow path exists through cannula 50, conduit 54 and conduit 55 to the interior of the pump means. The cannula means of the present invention includes a second cannula 56 having a sharpened tip 58 at one end. Cannula 50 and cannula 56 are oriented parallel to each other. When the apparatus of the present invention is first assembled, sharpened tip 58 is positioned within seal 38. Cannula 56 extends through an elongated bore in the body 34 and cannula 56 is connected to a delivery conduit or delivery tube 60 which extends from a second end 62 of the second cannula, along the interior of the wall 42 toward the top 44 of wall 42. The delivery conduit 60 is positioned adjacent elongated slot 46 but is longer than the slot and is prevented from moving into or through the slot by contact between the delivery conduit and the pump means and the wall.

An uptake conduit 64 is provided for the test tube, the uptake conduit including a float 66 positioned interiorly of the test tube and the uptake conduit is connected to a bore in the test tube stopper 12. Since stopper 12 is formed of a resilient, self-sealing, repuncturable material such as rubber, a short tube or cannula may be utilized as a conduit 68 rather than a bore in the stopper.

The apparatus of the present invention is intended to be assembled to the test tube or blood collection tube at the time that the test tube is placed under partial vacuum.

The operation of the apparatus will now be explained. When it is desired to withdraw biological fluid from a patient, the test tube, with the apparatus of the present invention attached, is inserted into a conventional multiple draw collection tube holder means 70 of the type having a closed first end 72 and an open second end 74 with an exterior flange 75 intermediate the first and second ends. The flange provides for holding the holder during use. The holder includes a cannula 76 extending through the closed end 72, the cannula having a first sharpened end 78 exteriorly of the holder and a second sharpened end 80 positioned interiorly of the holder. The test tube and apparatus of the present invention is inserted into the open second end 74 of the holder and moved axially inwardly in a manner similar to the installation of a conventional test tube into a multiple draw collection tube holder. The relative axial movement causes cannula 76, and specifically sharpened end 80, to enter through the aperture 25 in the pump means, through the interior of the pump means, through a suitable bore 82 in the housing means plug 32, through the seal 38, and through the test tube stopper 12, thus providing access to the interior of the test tube. As the height of body 34 exceeds the height of the pump, upon insertion the top 44 of the body 34 contacts the interior closed end 72 thus preventing accidental actuation of the pump while the apparatus is in the holder 70. Once the cannula 76 is positioned as described, biological fluid from a patient will enter the sharpened tip 78 of cannula 76 and flow through cannula 76 into the test tube.

After the completion of withdrawal of biological fluid from the patient (and the sharpened cannula tip 78 withdrawn from the patient) holder 70 with the cannula 76 therein may be removed from the apparatus and discarded. Then the test tube, with the pump means 24 attached, may be subjected to centrifuging or other processing. The axial length of the holder 70, from flange 75 to end 72, may be longer than a conventional holder to accommodate the pump means and holder of the present invention.

When it is desired to remove aliquots of biological fluid from the test tube, the apparatus of the present invention must be initially activated. This is accomplished by covering the pump vent aperture 25 and compressing the pump means, or bellows, from the first end 26 toward the second end 28 a sufficient distance to accomplish the following. The axially downward movement of the pump will cause contact between the pump first end 26 and the body 34. Continued axial downward movement of the pump will move the body 34, from a first or rest position, axially downwardly toward the test tube stopper. This movement of the body will cause tip 52 of cannula 50 to pierce through the stopper 12 and enter the air gap 20 within the test tube. The movement of the body 34 will also cause cannula 56 to move downwardly until tip 58 pierces through the seal 38 and enters the cavity 40. Finally, the movement of the plug 34 and cannula 56 downwardly will move the delivery conduit 60 (which is attached to cannula 56) downwardly from a stored position until the flexible delivery conduit 60 pivots outwardly through the slot 46 in the wall 42 of the housing, which may be considered an "active" position. Thus, the body 34 is moved axially to a second position.

Next, the pump means of the present invention is released and returns to its initial position, and ambient air enters through the vent 25. Vent 25 is then covered and pump means again actuated. Air within the pump means flows through conduits 54 and 55 and through cannula 50 to the interior of the test tube. This pressurizes the air within the test tube and, in response to the pressure, serum flows up the uptake conduit 64 and conduit 68 into the cavity 40. From the cavity 40, the serum (or other fluid within the test tube) flows through cannula 56 and delivery conduit 60 and is dispensed, in a drop-by-drop manner, through the delivery conduit 60. In this regard, arrows 83 illustrate the fluid flow in FIG. 5. The rate of dispensing biological fluid may be controlled by the rate of flexing (compression and release) of the flexible member or bellows and by the degree of force applied during such flexing or pumping operation. Release of the bellows or pump vent aperture 25 allows ambient air to be drawn into the pump for successive pumping operations.

Referring to FIG. 6, an alternate embodiment of the present invention is illustrated. One difference between the embodiment of FIG. 6 and the embodiment of FIGS. 1 and 3-5 is that a conduit 84, extending longitudinally from the cannula 50 through the body 34 opens into the interior of the pump. This replaces the two conduits 54, 55 previously described. A second aspect of the embodiment of FIG. 6 is that the cannula 50 and cannula 54 do not have sharpened tips. Rather, each cannula has a rounded tip 86, 88 respectively, and a transverse aperture 90, 92, respectively, through one wall of the cannula provides for fluid flow into or out of the cannula.

In the embodiment of FIG. 6, which forms a preferred embodiment the resilient test tube stopper (which is conventional in the other Figures) is formed of a specific configuration as follows. The stopper 94 is circular in plan view and includes a concave top section 95 to provide clearance for the movable plug 32, and a transverse slot 96, extending partially across the stopper, to function as the fluid transfer cavity 40. The portion of the stopper 94 above the slot 96 functions as the seal 38 of the prior embodiment. Further the stationary body and, in particular the lower end of the body is H-shaped in front elevation with the legs 98 of the "H" engaging the test tube at top of the stopper. The operation of this embodiment is the same as the operation of the prior embodiment.

According to the principles of the present invention, the seal 38 preferably may be formed of resealable rubber or material similar to that used as the conventional stopper for a test tube, as will stopper 94 in the embodiment of FIG. 6. Delivery conduit 60 and uptake conduit 64 may be formed of tetrafluoroethylene, and it may be appreciated that uptake conduit 64 includes a lower, partially coiled section attached to float 66. Fluid enters the coiled section of uptake conduit 64 in response to pressurized air in the test tube. Float 66, which is on top of the fluid in the test tube and moves therewith, automatically adjusts the vertical height of the bottom of uptake conduit 64 so that fluid, and not air, enters the conduit 64. Float 66 may be formed of polypropylene, plug 32 and body 34 (including wall 42) may be formed of styrene, and pump means 24 may be formed of polyethylene. All cannulas and conduit 68 may be formed of stainless steel. It should be appreciated that the foregoing identification of materials is illustrative only and should not be interpreted as limiting the present invention.

It will be understood that the above description of the present invention is susceptible to various modifications, changes, and adaptations, and the same are intended to be comprehended within the meaning and range of equivalents of the appended claims.

What is claimed is:

1. Apparatus for drawing biological fluid from a patient into a test tube, the test tube being sealed with a puncturable closure, and for thereafter dispensing the biological fluid through the closure and from the test tube comprising:
   pump means adapted to be connected to said test tube;
   housing means for said pump means; and
   cannula means having a first portion extending interiorly of said pump means and said housing means and having a tip insertable through said closure;
   said housing means having a first position for withdrawal of biological fluid from a patient, such that said biological fluid flows through said pump means and through said housing means into said sealed test tube; and
   said housing means having an second position for advancing said cannula means first portion tip through said closure such that upon actuation of said pump means, biological fluid is dispensed from said sealed test tube through said cannula means.

2. The apparatus of claim 1 wherein said housing means is attached to said test tube.

3. The apparatus of claim 1 including means for restricting accidental actuation of said pump means.

4. The apparatus of claim 1 wherein said housing means include means for restricting accidental actuation of said pump means.

5. A blood collection and delivery apparatus for attachment to a sealed test tube comprising:
   a housing assembly having a movable portion;
   pump means attached to said housing assembly for moving said housing assembly movable portion from a first position to a second position;
   said housing assembly first position for the withdrawal of biological fluid from a patient into said sealed test tube; and
   said housing assembly second position for the dispensing of biological fluid from said sealed test tube in response to actuation of said pump means after said pump means has first moved said housing assembly movable portion from said first position to said second position.

6. The apparatus of claim 5 wherein said pump means includes an extendable delivery conduit for dispensing of biological fluid therethrough.

7. The apparatus of claim 6 wherein said delivery conduit has a stored position and an active position.

8. The apparatus of claim 7 wherein movement of said housing assembly moves said delivery conduit from said stored position to said active position.

9. The apparatus of claim 6 including cannula means having a first portion movable from a rest position to an active position when said housing assembly movable portion is moved to said second position, and a second portion for providing biological fluid from said test tube to said delivery conduit in response to actuation of said pump means.

10. The apparatus of claim 9 wherein said cannula means second portion includes an uptake assembly positioned interiorly of said test tube.

11. The apparatus of claim 5 including a sealed test tube wherein biological fluid is introduced from a patient through said pump means and through said housing assembly and through said test tube seal into said test tube.

12. The apparatus of claim 5 including cannula means operatively coupled to said pump means, said pump means for pressurizing the interior of said test tube through said cannula means, and said cannula means for dispensing said biological fluid from the interior of said test tube, through said test tube seal.

13. The apparatus of claim 5 wherein said test tube has a longitudinal axis and said housing assembly movable portion moves along said longitudinal axis.

14. The apparatus of claim 5 including means for restricting accidental actuation of said pump means.

15. The apparatus of claim 5 wherein said housing means include means for restricting accidental actuation of said pump means.

16. The apparatus of claim 5 wherein the housing assembly has a wall having a height, said wall height exceeding the maximum height of said pump means.

17. The apparatus of claim 5 including a collection tube holder, wherein said housing assembly contacts the collection tube holder for preventing accidental activation of the pump.

18. A method of using the apparatus of claim 9 comprising the steps of:
attaching the apparatus to a sealed test tube;
withdrawing biological fluid from a patient through the pump means and through said housing into said sealed test tube;
actuating said pump means for moving said housing assembly movable portion from a first position to a second position, the second position for extending said delivery tube and for moving said first cannula portion through said test tube seal; and
actuating said pump means at least one additional time for pressurizing the contents of said test tube such that biological fluid flows from said test tube through said cannula means and said delivery tube.

19. A blood collection and delivery apparatus for attachment to a sealed test tube comprising:
a housing having an upper portion and a lower portion;
a movable body portion axially disposed within said housing, said movable body portion including an axial passageway for a flow of fluid therethrough;
pump means attached to said housing, said pump means being in fluid communication with said axial passageway;
cannula means including a first cannula attached to and extending through the movable body portion, said first cannula having a first end in fluid communication with the interior of said pump means and a second end for extending through said test tube seal to be in fluid communication with the interior of said test tube,
second cannula means including second cannula having a delivery tube, said delivery tube having a stored position within said housing and an active position extending through said housing, the movement of said housing body portion for moving said delivery tube from said stored position to said active position;
said second cannula means further including a conduit positioned interiorly of said test tube such that fluid from said test tube flows through said second cannula conduit and said delivery tube in response to pressure from said pump means after said housing body portion has been moved by said pump means.

20. A method of using a blood collection and delivery apparatus, the apparatus including a pump, a housing assembly with a moveable portion for said pump, a cannula operatively coupled to said pump and an extendable delivery tube for dispensing biological fluid therethrough, said method comprising the steps of:
attaching the apparatus to a sealed test tube;
withdrawing biological fluid from a patient through said pump and through said housing assembly into said sealed test tube;
actuating said pump for moving said housing assembly movable portion from a first position to a second position, the second position for extending said delivery tube and for moving said cannula through said test tube seal; and
actuating said pump at least one additional time for pressurizing the contents of said test tube such that biological fluid flows from said test tube through said cannula and said delivery tube.

* * * * *